United States Patent
Krieg et al.

(10) Patent No.: US 8,508,228 B2
(45) Date of Patent: Aug. 13, 2013

(54) LOCAL GRADIENT SYSTEM FOR IMAGING OF THE BREAST WITH PLANAR ARRANGEMENT

(75) Inventors: Robert Krieg, Nuremberg (DE); Sebastian Schmidt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 588 days.

(21) Appl. No.: 12/775,686

(22) Filed: May 7, 2010

(65) Prior Publication Data

US 2010/0283466 A1 Nov. 11, 2010

(30) Foreign Application Priority Data

May 7, 2009 (DE) .......................... 10 2009 020 361

(51) Int. Cl.
*G01V 3/00* (2006.01)

(52) U.S. Cl.
USPC .............................................. 324/318; 324/322

(58) Field of Classification Search
USPC .................. 324/300–322; 600/407–445
See application file for complete search history.

(56) References Cited

U.S. PATENT DOCUMENTS

| | | | |
|---|---|---|---|
| 5,534,778 A * | 7/1996 | Loos et al. .................... 324/318 |
| 6,144,204 A | 11/2000 | Sementchenko |
| 7,970,452 B2 * | 6/2011 | Piron et al. .................... 600/411 |
| 8,200,309 B2 * | 6/2012 | Wollin ........................ 600/407 |
| 2009/0082662 A1 * | 3/2009 | Israel ........................... 600/421 |
| 2011/0260727 A1 * | 10/2011 | Punchard et al. ............. 324/318 |
| 2012/0172704 A1 * | 7/2012 | Piron et al. .................... 600/410 |

* cited by examiner

*Primary Examiner* — Brij Shrivastav
(74) *Attorney, Agent, or Firm* — Schiff Hardin LLP

(57) ABSTRACT

A coil arrangement for a magnetic resonance tomography apparatus has plates that each contain at least one gradient coil.

16 Claims, 4 Drawing Sheets

LOCAL GRADIENT SYSTEM FOR IMAGING OF THE BREAST WITH PLANAR ARRANGEMENT

BACKGROUND OF THE INVENTION

1. Field of the Invention

The invention concerns a coil arrangement for a magnetic resonance tomography apparatus.

2. Description of the Prior Art

Magnetic resonance tomography apparatuses are known from DE 10 2005 052 564, for example.

In some applications of nuclear magnetic resonance tomography (MRT), steep and fast gradients would be advantageous; this applies to a particular degree to diffusion-weighted imaging. However, given the gradients used today very significant changes dB/dT or, respectively, dB/dX that can induce electrical currents in the nerve tracts are the result, the gradients are limited by the biological stimulation limit. In principle these limitations can be countered by local gradient systems.

From Parker/Hadley, Magnetic Resonance in Medicine 56:1251-1260 (2006) it is known that local gradients can help to overcome this problem.

An area of magnetic resonance tomography that is increasingly gaining importance is imaging of the female breast, in particular diffusion-weighted imaging. Here strong and fast gradients would be desirable, and in fact primarily in the medio-lateral (X) or anterior-posterior (Y) direction, since here the "decay" of the gradients to the base field strength ensues outside of the body of an examined patient, which is not possible in the Z-direction.

The use of a pot-shaped local gradient coil is known from MRM 39392-401 (1998), Maier et al. However, such a design has specific disadvantages: up, the breast of an examined patient is no longer accessible from the side in order to implemented biopsies, for example. A repositioning of the patient between diagnosis and biopsy is not an optimal solution, however, since the breast thereby shifts and subsequently a lesion can possibly no longer be unambiguously associated. Fixed anatomical landmarks that allow a registration of the images do not exist in the breast in practice.

SUMMARY OF THE INVENTION

It is an object of the invention to optimize the imaging of the female breast.

This object is achieved according to the invention by a method for SAR determination for a magnetic resonance tomography transmission system with multiple antenna elements (TxCh 1 through TxCH 8), wherein for multiple points in time or time periods the cross correlation matrix of an antenna element matrix of antenna element is respectively determined from antenna element field strength values of multiple antenna elements of the magnetic resonance tomography transmission system, wherein these cross correlation matrices are added up over a summation time period into a sum cross correlation matrix. The sum cross correlation matrix is multiplied with a HOTSPOT cross correlation sensitivity matrix, which HOTSPOT cross correlation sensitivity matrix represents the sensitivity in at least one direction at one of a plurality of hotspot points in an examination subject to be examined in a magnetic resonance tomography transmission system, wherein the product of the sum cross correlation matrix (TSUM) is multiplied with a HOTSPOT cross correlation sensitivity matrix and with a value representing the dielectricity at a hotspot point in order to determine a SAR value for this hotspot, wherein the voltage applied to antenna elements is reduced or deactivated upon the SAR value exceeding a predetermined upper limit.

One advantage relative to conventional gradient systems is that faster and steeper gradients can be generated, for example for diffusion-weighted imaging. One advantage relative to the "pot-shaped" design described in MRM 39392-401 (1998), Maier et al. is that the sides (the region between the plates) of the breast remain free so that a lateral and medial access is possible.

Since the relevant diffusion differences are not directed in tumor diagnostics (which is different than in neurological diagnostics), in principle a steep gradient in one spatial direction (as it can be achieved via opposite plates or plate pairs in this one direction) is sufficient.

If the gradient coils are arranged in the form of flat plates, in an examination these can respectively be situated cranial and caudal of (at least) one breast to be examined, and the lateral and medial region of the breast or breasts remains free.

A field gradient in the X-direction can advantageously be generated that has the form of an inverted "V" and whose maximum lies in the middle between the breasts, thus at a position at which no structures relevant to the imaging are situated. In contrast to "classical" MR tomography, in which the association of field strengths is subordinate to localization, here this is no longer the case. However, this problem can be solved in that local acquisition coils (for example coil arrays) are used and their "illumination profile" is taken into account so that the association is again bijective within the region "seen" by the acquisition coil.

The gradient system is advantageously integrated with acquisition coils, and according to one embodiment of the invention RF coils are also integrated into an arrangement that is portable and is only inserted into the MRT apparatus if a breast imaging is implemented.

If necessary the system can be extended with additional coils to generate a local gradient in the z-direction.

The system is advantageously combined with a biopsy device, for example a "grid" to set the biopsy coordinates. This can be arranged in the lateral free region of the gradient system without any problems.

The local gradient system can be used together with a conventional gradient system installed in the MRT apparatus, in particular if the local system is not in the position to generate gradients in arbitrary spatial directions.

DESCRIPTION OF THE PREFERRED EMBODIMENTS

Figure 1:
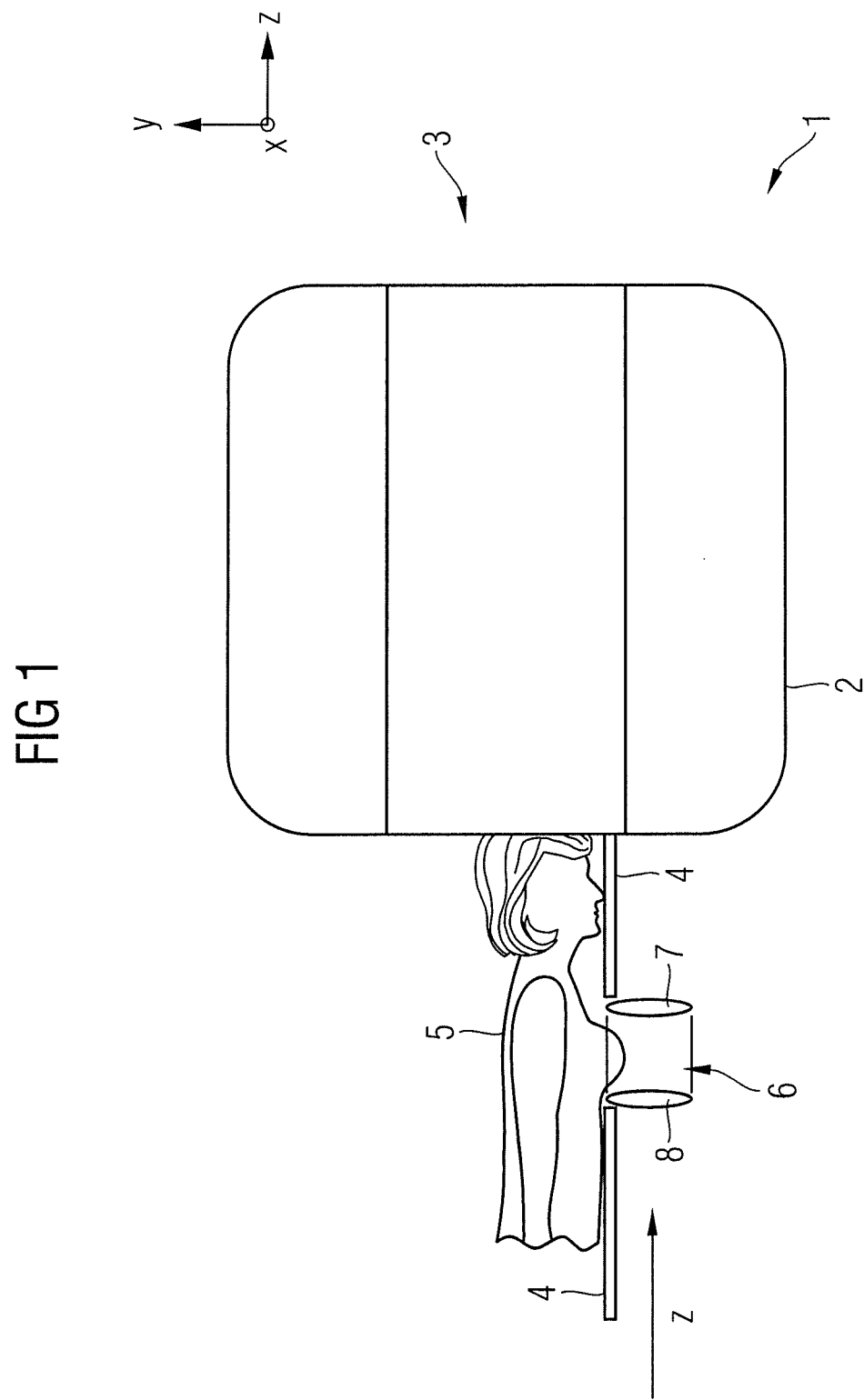
FIG. 1 schematically illustrates a magnetic resonance tomography apparatus.

FIG. 1 shows a magnetic resonance apparatus (MRT) 1 with a whole-body coil 2 and a tube-shaped space 3 into which a patient bed 4 (with a recess for a breast)—for example with a patient 5 and a coil arrangement 6 —can be driven in order to generate exposures of the patients 5 that can subsequently be processed further. Instead of a shown patient bed 4 with a recess for a breast, the patient can also lie on her back on a patient bed, for example. The shown directions in FIG. 1 are medio-lateral (x), posterior-anterior (y) and caudal-cranial (z).

A coil arrangement 6 in the following in particular designates local gradient coils that could also be designated individually or together as a local gradient system.

Figure 2:
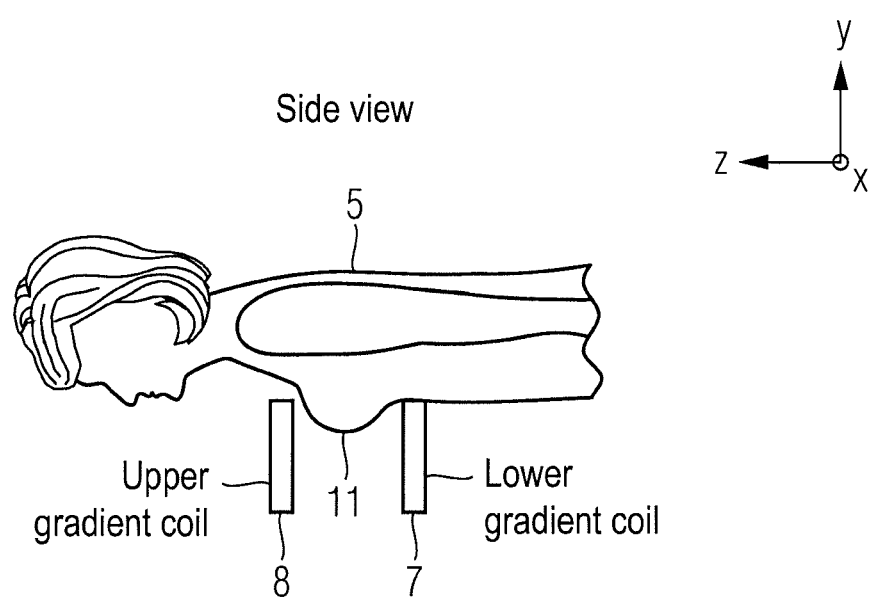
FIG. 2 is a sectioned side view of a patient and of plates with gradient coils.

FIG. 2 shows a sectioned side view of the patient 5.

Plates 7, 8 with gradient coils (not shown here) contained therein are arranged cranially (plate 8) and dorsally (plate 7) relative to (at least) one breast 11 of the patient 5.

Figure 3:
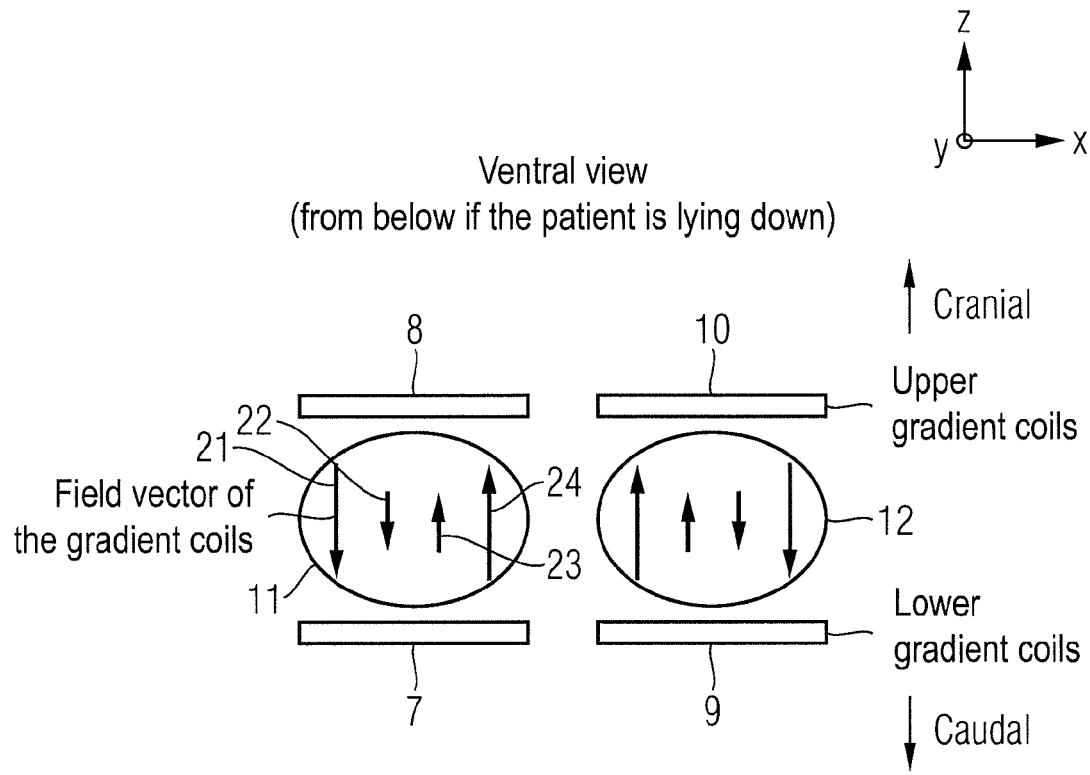
FIG. 3 is a cross-section through the patient and the coil arrangement.

FIG. 3 shows a cross section view through the breasts 11 and 12 of the patient (5).

The plate 7 (with gradient coils contained therein) is arranged caudal of the left breast 11. The plate 8 (with gradient coils contained therein) is arranged cranial of the left breast 11.

The plate 9 (with gradient coils contained therein) is arranged caudal of the right breast 12. The plate 10 (with gradient coils contained therein) is arranged cranial of the right breast 11.

Field vectors 21, 22, 23, 24 of the gradient coils 7, 8 in the breast 11 are shown for a few locations via arrows. Field vectors 31, 32, 33, 34 of the gradient coils 9, 10 in the breast 12 are also shown for a few locations via arrows. The fields of the gradient coils in the plates 7, 8 and the fields 31, 32, 33, 34 of the gradient coils in the plates 9, 10 add up to the field curve in FIG. 4.

Figure 4:
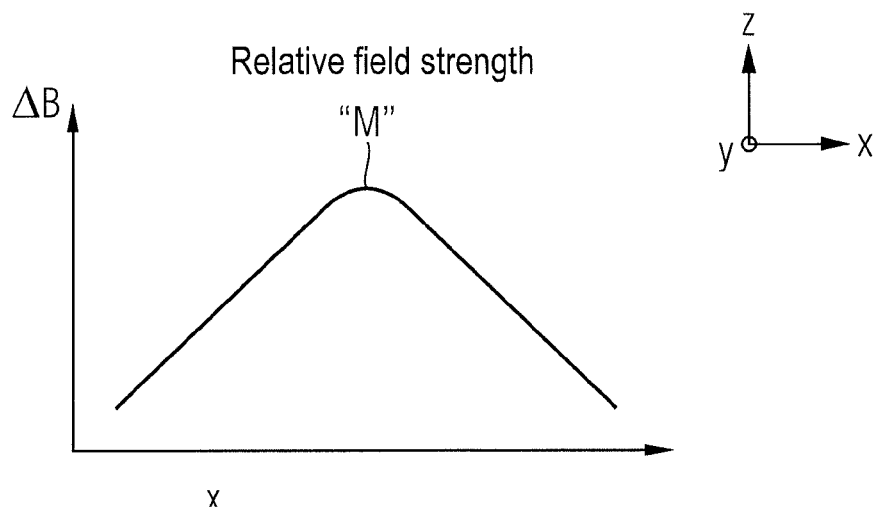
FIG. 4 shows an example of a curve of the magnitude of the relative field strength generated by gradient coils in plates in FIG. 3.

FIG. 4 shows a possible curve of the magnitude of the relative field strength B generated by gradient coils in plates (in FIG. 3) as a spatial curve in the medio-lateral direction (x) in FIG. 3 (shown above). A minimum of the V-shaped curve thus lies between the breasts, at which point a very high acquisition quality is, however, also not normally required.

Figure 5:
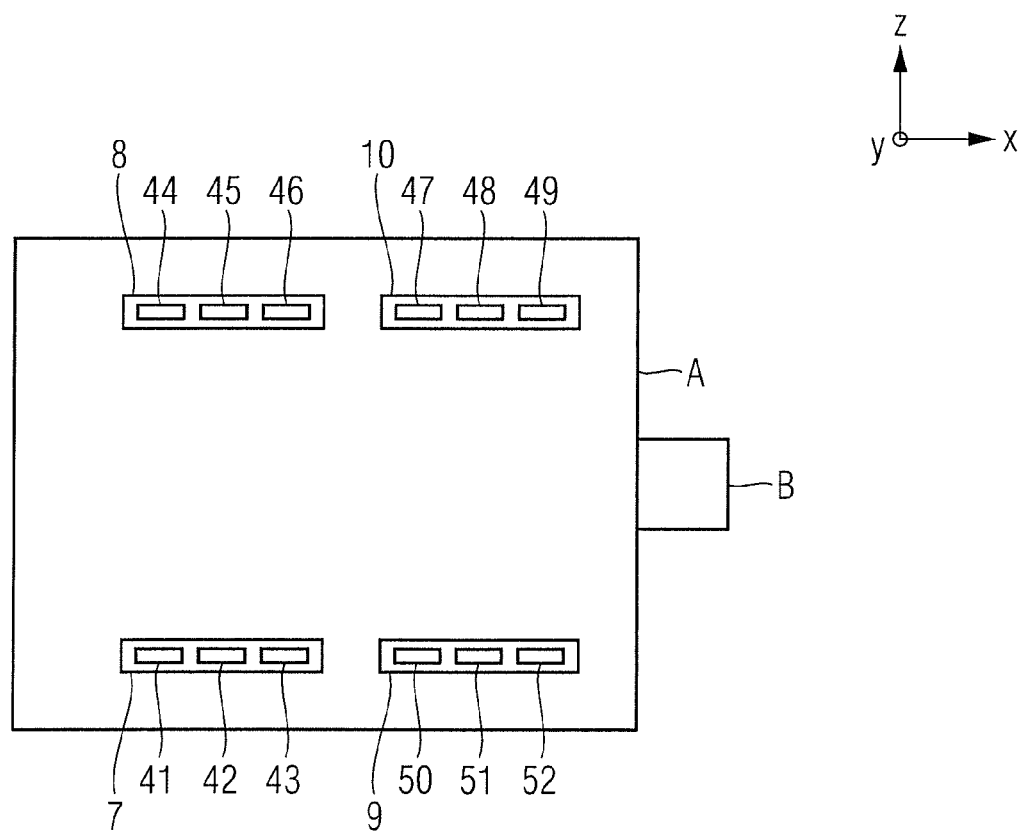
FIG. 5 is a cross-section through the patient and the coil arrangement in which gradient coils in the plates are also visible.

FIG. 5 shows a cross section view through the patient and the coil arrangement, in which view gradient coils 41, 43, 44, 46, 47, 49, 50, 52, acquisition coils 48, 51 and RF transmission coils 42, 45 are also schematically visible in the plates 7, 8, 9, 10 and a biopsy device B is schematically visible. Some or all components in FIG. 5 can be part of an arrangement A; this can also be wearable.

Although modifications and changes may be suggested by those skilled in the art, it is the intention of the inventors to embody within the patent warranted hereon all changes and modifications as reasonably and properly come within the scope of their contribution to the art.

We claim as our invention:

1. Coil arrangement for a magnetic resonance tomography apparatus, comprising:
   a plurality of gradient coils that generate a gradient field that participates in acquisition of magnetic resonance data from a predetermined region of a subject, said gradient coils having a coil configuration that generates said gradient field substantially only in a localized region that includes said examination region;
   a plurality of plates that each contain at least one of said gradient coils therein; and
   a housing in which said plates are mounted, said plates being mounted in said housing at respective locations to allow the gradient coils to generate said local gradient field substantially only in said examination region, and said plates being mounted in said housing at respective locations allowing at least one unobstructed access path to said examination region.

2. Coil arrangement according to claim 1, wherein the plates are flat.

3. Coil arrangement according to claim 1, wherein two of said plates are arranged in a plane.

4. Coil arrangement according claim 1 wherein two of said plates are respectively arranged in two planes.

5. Coil arrangement according to claim 1, wherein said plates are configured for cranial and caudal placement relative to a breast to be examined.

6. Coil arrangement according to claim 1, wherein the plates are configured for an examination of a breast, forming a breast coil arrangement.

7. Coil arrangement according to claim 1, comprising plates that are opposite in only one spatial direction, with which plates a gradient field is produced in this spatial direction.

8. Coil arrangement according to claim 1, wherein a gradient field is generated by two plates arranged in a plane, said field having a magnitude maximum in a plane of application between the plates.

9. Coil arrangement according to claim 1, wherein a gradient field is generated by two plates arranged in a plane, that increases in the region of one plate in the direction of the other plate.

10. Coil arrangement according to claim 1, wherein a spatial region detected by one acquisition coil is taken into account to determine the location of the coil arrangement or of a plate of the coil arrangement.

11. Coil arrangement according to claim 1, also comprising at least one acquisition coil.

12. Coil arrangement according to claim 1, also comprising at least one RF transmission coils.

13. Coil arrangement according to claim 1, wherein the gradient coils contained in the plates are configured to generate a gradient field in a direction of a breast to be examined.

14. Coil arrangement according to claim 13, wherein the gradient coils contained in the plates are configured to generate an additional gradient field orthogonal to the gradient field in the direction of the breast.

15. Coil arrangement according to claim 1, wherein every other plate is arranged opposite one another in the caudal-cranial direction.

16. Coil arrangement according to claim 1, comprising a biopsy device in the lateral region of the coil arrangement.

* * * * *